US012763133B2

(12) United States Patent
Parekh et al.

(10) Patent No.: US 12,763,133 B2
(45) Date of Patent: Oct. 13, 2026

(54) MEMORY DIE AND LOGIC DIE WITH WAFER-ON-WAFER BOND

(71) Applicant: Micron Technology, Inc., Boise, ID (US)

(72) Inventors: Kunal R. Parekh, Boise, ID (US); Sean S. Eilert, Penryn, CA (US); Aliasger T. Zaidy, Seattle, WA (US); Glen E. Hush, Boise, ID (US)

(73) Assignee: Micron Technology, Inc., Boise, ID (US)

( * ) Notice: Subject to any disclaimer, the term of this patent is extended or adjusted under 35 U.S.C. 154(b) by 612 days.

(21) Appl. No.: 17/884,781

(22) Filed: Aug. 10, 2022

(65) Prior Publication Data

US 2023/0048103 A1 Feb. 16, 2023

Related U.S. Application Data

(60) Provisional application No. 63/231,660, filed on Aug. 10, 2021.

(51) Int. Cl.
*G11C 11/4093* (2006.01)
*G06F 3/06* (2006.01)
(Continued)

(52) U.S. Cl.
CPC ........ *G11C 11/4093* (2013.01); *G06F 3/0656* (2013.01); *G06F 13/1673* (2013.01);
(Continued)

(58) Field of Classification Search
CPC ..... G11C 11/4093; G11C 7/08; G11C 7/1039; G11C 11/4087; G11C 11/4091; G11C 11/4096; G16B 50/10; G16B 30/00; G06F 2213/28; G06F 3/0656; G06F 13/1673; G06F 13/28; H01L 21/78; H01L 22/12; H01L 24/08; H01L 24/48; H01L 24/80; H01L 25/0652; H01L 25/0657; H01L 25/18; H01L 25/50; H01L 24/16; H01L 2224/0801; H01L 2224/08145; H01L 2224/1601; H01L 2224/16221; H01L 2224/48091; H01L 2224/48145; H01L 2224/48221; H01L 2224/80895;
(Continued)

(56) References Cited

U.S. PATENT DOCUMENTS 8,930,647 B1 * 1/2015 Smith ................ G06F 12/0811
711/E12.008
9,432,298 B1 * 8/2016 Smith ................ H04L 49/9057
(Continued)

FOREIGN PATENT DOCUMENTS

CN 110265292 9/2019

*Primary Examiner* — Jeff W Natalini
*Assistant Examiner* — Andrew John Zabel
(74) *Attorney, Agent, or Firm* — Brooks, Cameron & Huebsch, PLLC

(57) ABSTRACT

Methods, systems, and devices related to a memory die and a logic die having a wafer-on-wafer bond therebetween. A memory die can include a memory array and a plurality of input/output (IO) lines coupled thereto. A logic die can include a deep learning accelerator (DLA). The memory die can be coupled to the logic die by a wafer-on-wafer bond. The wafer-on-wafer bond can couple the plurality of IO lines to the DLA.

17 Claims, 9 Drawing Sheets

(51) Int. Cl.

| | |
|---|---|
| ***G06F 13/16*** | (2006.01) |
| ***G06F 13/28*** | (2006.01) |
| ***G11C 7/08*** | (2006.01) |
| ***G11C 7/10*** | (2006.01) |
| ***G11C 11/408*** | (2006.01) |
| ***G11C 11/4091*** | (2006.01) |
| ***G11C 11/4096*** | (2006.01) |
| ***G16B 30/00*** | (2019.01) |
| ***G16B 50/10*** | (2019.01) |
| ***H10P 54/00*** | (2026.01) |
| ***H10P 74/20*** | (2026.01) |
| ***H10W 72/00*** | (2026.01) |
| ***H10W 72/20*** | (2026.01) |
| ***H10W 72/50*** | (2026.01) |
| ***H10W 72/90*** | (2026.01) |
| ***H10W 80/00*** | (2026.01) |
| ***H10W 90/00*** | (2026.01) |
| ***H10W 99/00*** | (2026.01) |
| *H10W 90/20* | (2026.01) |
| *H10W 90/26* | (2026.01) |

(52) U.S. Cl.

CPC ................ *G06F 13/28* (2013.01); *G11C 7/08* (2013.01); *G11C 7/1039* (2013.01); *G11C 11/4087* (2013.01); *G11C 11/4091* (2013.01); *G11C 11/4096* (2013.01); *G16B 30/00* (2019.02); *G16B 50/10* (2019.02); *H10P 54/00* (2026.01); *H10P 74/203* (2026.01); *H10W 72/50* (2026.01); *H10W 72/90* (2026.01); *H10W 90/00* (2026.01); *H10W 99/00* (2026.01); *G06F 2213/28* (2013.01); *H10W 72/01* (2026.01); *H10W 72/07252* (2026.01); *H10W 72/20* (2026.01); *H10W 72/221* (2026.01); *H10W 80/312* (2026.01); *H10W 80/327* (2026.01); *H10W 80/721* (2026.01); *H10W 90/20* (2026.01); *H10W 90/26* (2026.01); *H10W 90/288* (2026.01); *H10W 90/297* (2026.01); *H10W 90/721* (2026.01); *H10W 90/724* (2026.01); *H10W 90/751* (2026.01); *H10W 90/752* (2026.01); *H10W 90/792* (2026.01)

(58) Field of Classification Search

CPC . H01L 2224/80896; H01L 2225/06517; H01L 2225/06524; H01L 2225/06527; H01L 2225/06541; H01L 2225/06565; H01L 2225/06589; H01L 2924/1431; H01L 2924/14335; H01L 2924/1436

See application file for complete search history.

(56) References Cited

U.S. PATENT DOCUMENTS

| | | | | |
|---|---|---|---|---|
| 10,147,676 | B1 * | 12/2018 | Cox | H01L 24/16 |
| 11,430,766 | B2 | 8/2022 | Liu et al. | |
| 11,769,731 | B2 * | 9/2023 | Yu | H10P 72/74<br>257/690 |
| 2014/0176187 | A1 * | 6/2014 | Jayasena | G06F 15/7867<br>326/39 |
| 2014/0181417 | A1 * | 6/2014 | Loh | H01L 25/18<br>711/141 |
| 2015/0016172 | A1 * | 1/2015 | Loh | G06F 3/0608<br>365/51 |
| 2020/0161242 | A1 | 5/2020 | Lin et al. | |
| 2020/0202939 | A1 * | 6/2020 | Hush | G06F 17/16 |
| 2020/0203364 | A1 * | 6/2020 | Totoki | H10B 41/35 |
| 2020/0243486 | A1 | 7/2020 | Quader et al. | |
| 2020/0272344 | A1 * | 8/2020 | Murphy | G06F 3/0679 |
| 2020/0303343 | A1 | 9/2020 | Manipatruni et al. | |
| 2021/0043557 | A1 | 2/2021 | Lee et al. | |
| 2021/0118890 | A1 | 4/2021 | Kim et al. | |
| 2021/0175211 | A1 | 6/2021 | Liu et al. | |
| 2022/0044107 | A1 * | 2/2022 | Kale | G06F 3/0679 |
| 2022/0044108 | A1 * | 2/2022 | Kale | G06N 3/04 |
| 2022/0129196 | A1 * | 4/2022 | Roberts | G06F 3/065 |
| 2022/0147809 | A1 * | 5/2022 | Zaidy | G06N 3/08 |
| 2022/0342595 | A1 * | 10/2022 | Chatterjee | G06F 3/0659 |

* cited by examiner

MEMORY DIE AND LOGIC DIE WITH WAFER-ON-WAFER BOND

PRIORITY INFORMATION

This application is a non-provisional application of U.S. Application No. 63/231,660, filed Aug. 10, 2021, the contents of which are included herein by reference.

TECHNICAL FIELD

The present disclosure relates generally to memory, and more particularly to apparatuses and methods associated with memory die and logic die with wafer-on-wafer bond.

BACKGROUND

Memory devices are typically provided as internal, semiconductor, integrated circuits in computers or other electronic devices. There are many different types of memory including volatile and non-volatile memory. Volatile memory can require power to maintain its data and includes random-access memory (RAM), dynamic random access memory (DRAM), and synchronous dynamic random access memory (SDRAM), among others. Non-volatile memory can provide persistent data by retaining stored data when not powered and can include NAND flash memory, NOR flash memory, read only memory (ROM), Electrically Erasable Programmable ROM (EEPROM), Erasable Programmable ROM (EPROM), and resistance variable memory such as phase change random access memory (PCRAM), resistive random access memory (RRAM), and magnetoresistive random access memory (MRAM), among others.

Memory is also utilized as volatile and non-volatile data storage for a wide range of electronic applications including, but not limited to personal computers, portable memory sticks, digital cameras, cellular telephones, portable music players such as MP3 players, movie players, and other electronic devices. Memory cells can be arranged into arrays, with the arrays being used in memory devices.

DETAILED DESCRIPTION

Figure 1:
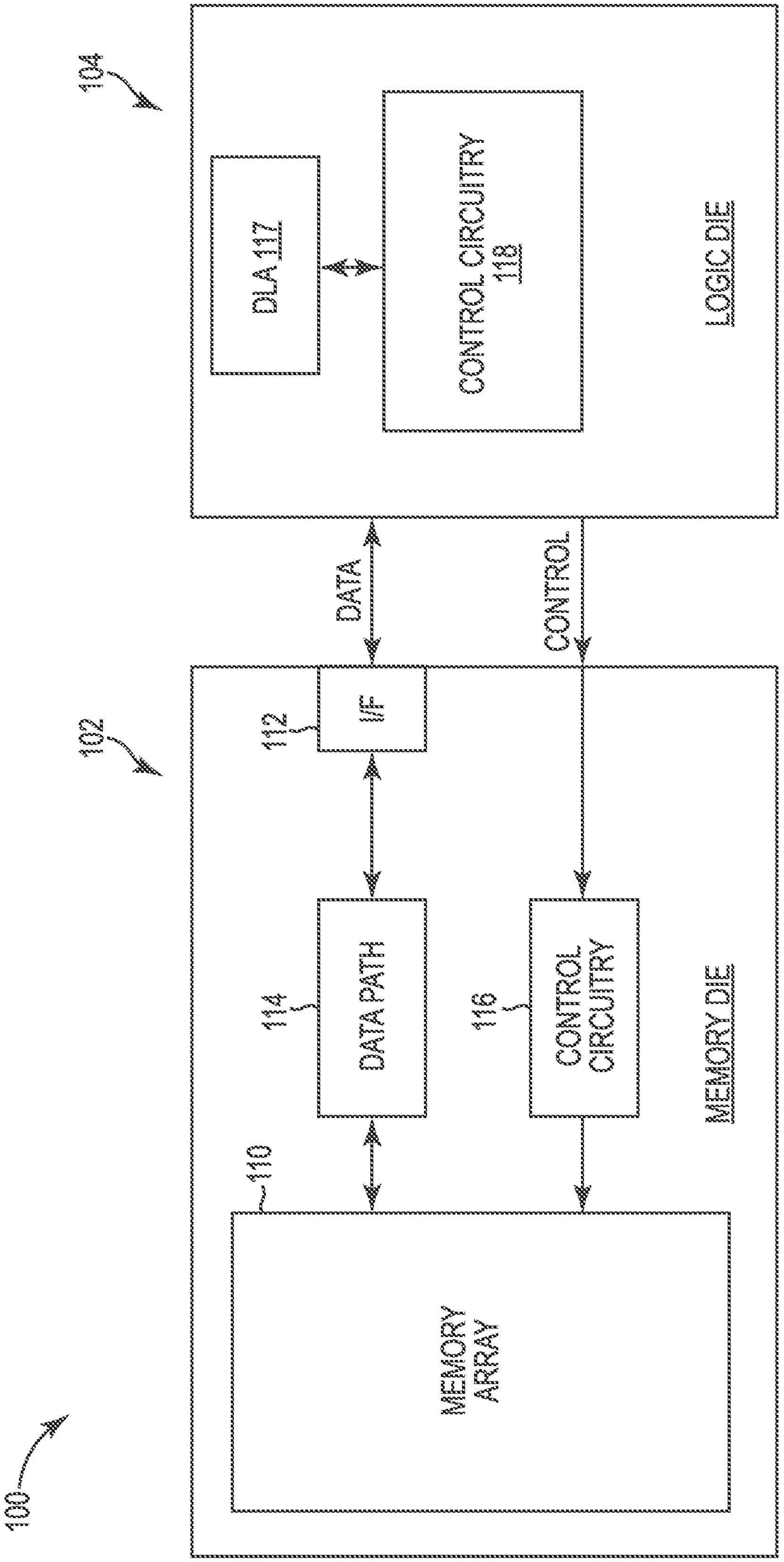
FIG. 1 illustrates a block diagram of an apparatus in the form of a system including a memory die and a logic die in accordance with a number of embodiments of the present disclosure.

The present disclosure includes apparatuses and methods related to a package including a memory device and a logic device with a wafer-on-wafer bond. Inexpensive and energy-efficient logic circuitry has been proposed, which can benefit from being tightly coupled to memory devices. Logic devices can be accelerators. Accelerators, which can be resident on a logic die, can include artificial intelligence (AI) accelerators such as deep learning accelerators (DLAs). As used herein, “resident on” refers to something that is physically located on a particular component. The term “resident on” can be used interchangeably with other terms such as “deployed on” or “located on,” herein. AI refers to the ability to improve a machine through “learning” such as by storing patterns and/or examples which can be utilized to take actions at a later time. Deep learning refers to a device’s ability to learn from data provided as examples. Deep learning can be a subset of AI. Neural networks, among other types of networks, can be classified as deep learning. The low power, inexpensive design of deep learning accelerators can be implemented in internet-of-things (IoT) devices. The DLAs can process and make intelligent decisions at run-time. Memory devices including the DLAs can also be deployed in remote locations without cloud or offloading capability.

A three-dimensional integrated circuit (3-D IC) is a metal-oxide semiconductor (MOS) IC manufactured by stacking semiconductor dies and interconnecting them vertically using, for example, through-silicon vias (TSVs) or metal connections, to function as a single device to achieve performance improvements at reduced power and smaller footprint than conventional two-dimensional processes. Examples of 3-D ICs include hybrid memory cube (HMC) and high bandwidth memory (HBM), among others.

Implementations of AI, such as a DLA, can include performing large quantities (e.g., thousands) of computations in parallel and large quantities of iterations thereof. The phrase “in parallel” can be used herein as a synonym for concurrent. Signals indicative of data can be input to a DLA from a memory device coupled thereto. The amount of data that can be input to a DLA in parallel may be a limitation on a rate at which the DLA can perform computations. Thus, it can be beneficial to increase the amount of data input to a DLA in parallel.

Some previous approaches to increase the amount of data input to a DLA in parallel may include increasing the quantity of interconnects (e.g., jumpers) coupling a memory device to the DLA. However, this requires an increase in the size of the memory die on which the memory device resides. Some previous approaches may include components, such as transistors, on data paths on the memory die from the memory device to the DLA.

Implementing a memory device in which memory die and logic die are coupled using a wafer-on-wafer bond can benefit from efficient transfer of data between the memory die and the logic die. Transferring data from the memory die to the logic die can include transferring data from the memory die to a global data bus and transferring the data from the global data bus to the logic die. However, transferring data from the global data bus to the logic die may be inefficient.

Aspects of the present disclosure address the above and other deficiencies of previous approaches. Some embodiments of the present disclosure include forming a wafer-on-wafer bond between a first wafer including memory dies and a second wafer including logic dies, such that at least one of the memory dies is aligned with and coupled to at least one of the logic dies. Such embodiments can increase bandwidth between the memory die and the logic die, which can include a DLA. A wafer-on-wafer bond, in accordance with the present disclosure, does not require an increase in size of the memory die or the logic die. The wafer-on-wafer bond can allow for more precisely controlled alignment of the memory dies and logic dies than can be achieved via chip-to-chip bonding. For example, the wafer-on-wafer bond can allow for such fine pitch control as to allow for individual local input/output lines of the memory die to be connected to input circuitry of the logic die, as described in further detail herein.

In some embodiments forming a wafer-on-wafer bond can include arranging a memory die face-to-face with a logic die. A face-to-face orientation or arrangement refers to respective substrates (wafers) being both distal to a wafer-on-wafer bond while a memory die and a logic die are proximal to the wafer-on-wafer bond. In some embodiments, forming a wafer-on-wafer bond between a memory die and a logic die can include forming one or more metal materials that couples the memory die to the logic die. In at least one embodiment, the wafer-on-wafer bond can comprise only metal materials. Data paths between a memory die and a logic die provided by the wafer-on-wafer bond can be on-pitch with memory cells of the memory die.

As used herein, the singular forms "a," "an," and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." As used herein, "coupled to" or "coupled with" generally refers to a connection between components, which can be an indirect communicative connection or direct communicative connection (e.g., without intervening components), whether wired or wireless, including connections such as electrical, optical, magnetic, and the like. As used herein, "a number of" something can refer to one or more of such things. For example, a number of memory devices can refer to one or more memory devices. A "plurality" of something intends two or more.

The figures herein follow a numbering convention in which the first digit or digits correspond to the drawing figure number and the remaining digits identify an element or component in the drawing. Similar elements or components between different figures may be identified by the use of similar digits. For example, 102 references element "02" in FIG. 1, and a similar element is referenced as 202 in FIG. 2A. Analogous elements within a figure may be referenced with a hyphen and extra numeral or letter. See, for example, elements 419-1 and 419-2 in FIG. 4. As will be appreciated, elements shown in the various embodiments herein can be added, exchanged, and/or eliminated so as to provide a number of additional embodiments of the present disclosure. In addition, as will be appreciated, the proportion and the relative scale of the elements provided in the figures are intended to illustrate certain embodiments of the present invention and should not be taken in a limiting sense.

FIG. 1 illustrates a block diagram of an apparatus in the form of a system 100 including a memory die 102 and a logic die 104 in accordance with a number of embodiments of the present disclosure. As used herein, a memory die 102, memory array 110, and/or a logic die 104, for example, might also be separately considered an "apparatus.

As illustrated by FIG. 1, the system 100 includes a memory die 102 coupled to a logic die 104. The memory die 102 can include an interface (I/F) 112 (e.g., an input/output (IO) I/F). The system 100 can be coupled to a host, such as a personal laptop computer, a desktop computer, a digital camera, a mobile telephone, a memory card reader, a server, a vehicle, or an IoT enabled device among various other types of hosts.

The logic die 104 can include a logic device, such as AI circuitry. The AI circuitry can be an AI accelerator, which is also referred to herein as a DLA 117. The DLA 117 can be coupled to the IO circuitry 112 and thus to a data path 114, which is coupled to a memory device, such as memory array 110. In some embodiments, the logic die 104 can be bonded to the memory die 102. In some embodiments, boding the logic die 104 to the memory die 102 can include bonding the DLA 117 to the memory array 110. The logic die 104 can include control circuitry 118. The control circuitry 118 can control transceivers of the memory die 102 to communicate data from the memory die 102 to the logic die 104 (e.g., via TSVs that couple the memory die to the logic die) and/or from the logic die 104 to the memory die 102. The DLA 117 can be coupled to the control circuitry 118. In some embodiments, the control circuitry 118 can control the DLA 117. For example, the control circuitry 118 can provide signaling to control circuitry 116, a row decoder (not illustrated), and/or a column decoder (not illustrated) of the memory die 102 to direct communication of data from the memory array 110 to the DLA 117. The data can be provided as an input to the DLA 117 and/or an artificial neural network (ANN) hosted by the DLA 117. The control circuitry 118 can cause the output of the DLA 117 and/or the ANN to be provided to the I/F 112 and/or stored to the memory array 110.

An ANN model can be trained by the DLA 117, the control circuitry 118, and/or by a host. For example, a host and/or the control circuitry 118 can train an ANN model, which can be provided to the DLA 117. The DLA 117 can implement the trained ANN model as directed by the control circuitry 118. The ANN model can be trained to perform a desired function. Non-limiting examples of implementations of the system 100 include digital signal processors (DSPs), graphics processing units (GPUs), systems on chip (SoCs), 5G antennas, safety monitoring, biometrics (e.g., facial recognition), data center network switches, autonomous vehicles, hardware accelerators for genomics, proteinomics, and/or gene sequencing, augmented virtual reality, blockchains, and streaming devices (provides local processing).

For clarity, the system 100 has been simplified to focus on features with particular relevance to the present disclosure. Non-limiting examples of the memory array 110 include a DRAM array, SRAM array, STT RAM array, PCRAM array, TRAM array, RRAM array, NAND flash array, NOR flash array, and/or 3DXPoint array. The memory array 110 can be referred to herein as a DRAM array as an example. The memory array 110 can comprise memory cells arranged in rows coupled by access lines (which may be referred to herein as word lines or select lines) and columns coupled by sense lines (which may be referred to herein as digit lines or data lines). Although the memory array 110 is shown as a single memory array, the memory array 110 can represent a plurality of memory arrays arranged in banks of the memory die 102.

Although not specifically illustrated, the memory die 102 can include address circuitry to latch address signals provided over a host interface. With respect to the system 100, the host (not illustrated) is a device different than the memory die 102 and the logic die 104 that can be coupled to either or both of the memory die 102 and the logic die 104. The host interface can include, for example, a physical interface (e.g., a data bus, an address bus, and a command bus, or a combined data/address/command bus) employing a suitable protocol. Such protocol may be custom or proprietary, or the host interface may employ a standardized protocol, such as Peripheral Component Interconnect Express (PCIe), Gen-Z interconnect, cache coherent interconnect for accelerators (CCIX), or the like. Address signals are received and decoded by a row decoder and a column decoder to access the memory array 110. Data can be read from the memory array 110 by sensing voltage and/or current changes on the sense lines using sensing circuitry. The sensing circuitry can be coupled to the memory array 110. Each memory array 110 and corresponding sensing circuitry can constitute a bank of the memory die 102. The sensing circuitry can comprise, for example, sense amplifiers that can read and latch a page (e.g., row) of data from the memory array 110. The I/F 112 can be used for bi-directional data communication with the logic die 104 along the data path 114. Read/write circuitry can be used to write data to the memory array 110 and/or read data from the memory array 110. The read/write circuitry can include various drivers, latch circuitry, etc.

The control circuitry 116 (e.g., a local controller) of the memory die can decode signals provided by a host (not illustrated. Signals from a host can be indicative of commands, for instance. These signals can include chip enable signals, write enable signals, and address latch signals that are used to control operations performed on the memory array 110, including data read operations, data write operations, and data erase operations. In some embodiments, the control circuitry 116 can be responsible for executing instructions from the host. The control circuitry 116 can comprise a state machine, a sequencer, and/or some other type of control circuitry, which may be implemented in the form of hardware, firmware, or software, or any combination thereof. Data can be provided to the logic die 104 and/or from the logic die 104 via data lines coupling the logic die 104 to the I/F 112.

According to some previous approaches, after fabrication of the electronic devices (e.g., the memory array 110 and the DLA 117) on a first wafer and a second wafer, the first wafer and the second wafer can be diced (e.g., by a rotating saw blade cutting along streets of the first wafer and the second wafer) to form the memory die 102 and the logic die 104, respectively. However, according to at least one embodiment of the present disclosure, after fabrication of the devices on the first wafer and the second wafer, and prior to dicing, the first wafer and the second wafer can be bonded together by a wafer-on-wafer bonding process. Subsequent to the wafer-on-wafer bonding process, the dies (e.g., the memory die 102 and the logic die 104) can be singulated. As used herein, "singulate" refers to separating conjoined units into individual units. For example, a memory wafer can be bonded to a logic wafer in a face-to-face orientation meaning that their respective wafers (substrates) are both distal to the bond while the memory dies and logic dies are proximal to the bond. This enables individual memory die and logic die to be singulated together as a single package after the memory wafer and the logic wafer are bonded together.

Figure 2A:
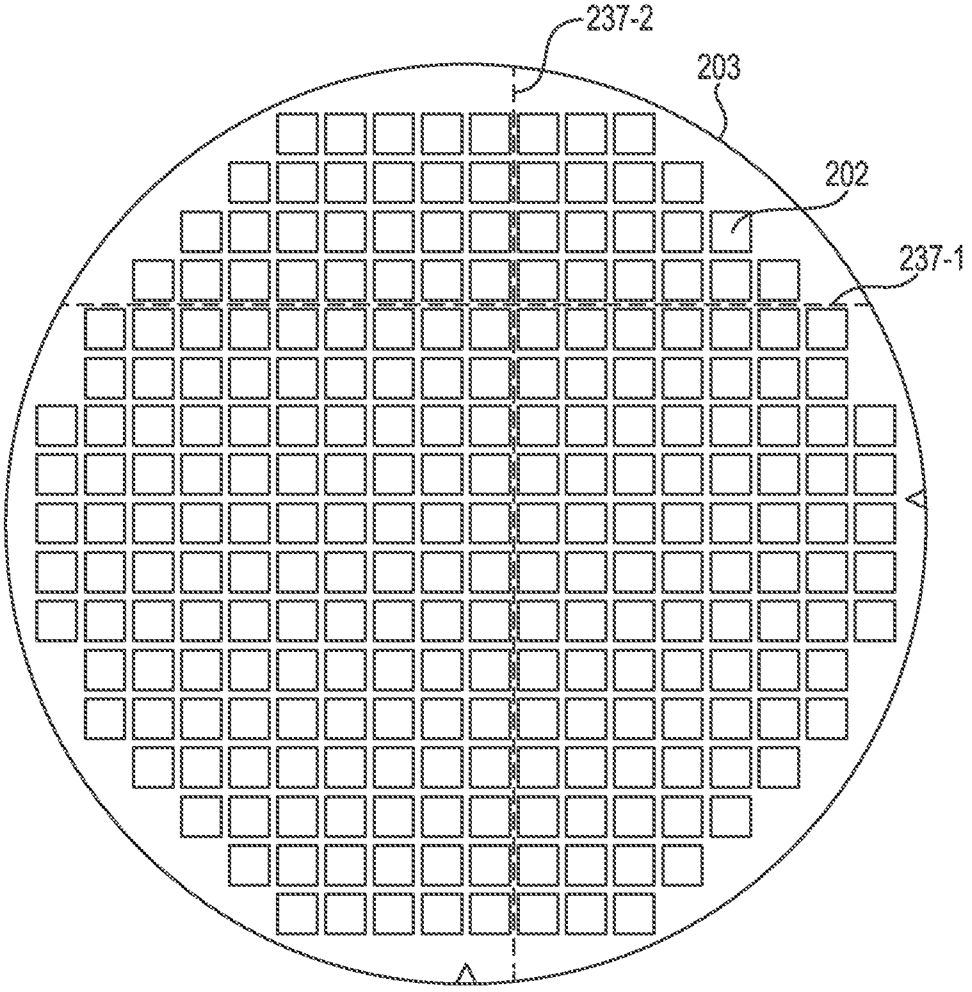
FIG. 2A is a top view of a memory wafer in accordance with a number of embodiments of the present disclosure.
Figure 2B:
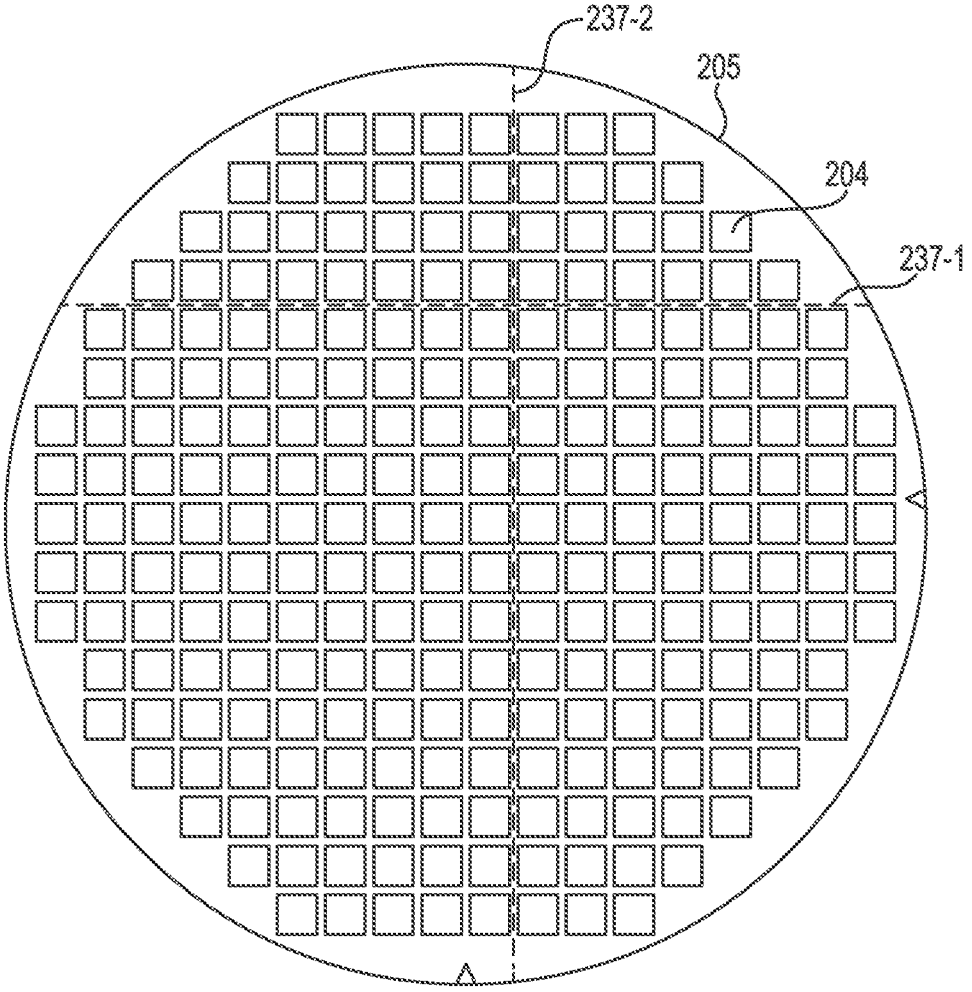
FIG. 2B is a top view of a logic wafer in accordance with a number of embodiments of the present disclosure.

FIG. 2A is a top view of a memory wafer 203 in accordance with a number of embodiments of the present disclosure. FIG. 2B is a top view of a logic wafer 205 in accordance with a number of embodiments of the present disclosure. The memory die 202 and the logic die 204 can be analogous to the memory die 102 and the logic die 104, respectively, described in association with FIG. 1. The memory wafer 203 and/or the logic wafer 205 can include, but is not limited to, silicon-on-insulator (SOI) or silicon-on-sapphire (SOS) technology, doped and undoped semiconductors, epitaxial layers of silicon supported by a base semiconductor foundation, and other semiconductor structures.

As illustrated in FIGS. 2A-2B, the memory wafer 203 and/or the logic wafer 205 can have a round peripheral edge. The memory wafer 203 and/or the logic wafer 205 can include a number of dies (e.g., the memory die 202 illustrated in FIG. 2A or the logic die 204 illustrated in FIG. 2B) having streets 237 (e.g., the streets 237-1 and 237-2) located therebetween. The streets 237 may be referred to as saw streets or scribe streets herein. The streets 237 can be paths along which a tool may cut in order to singulate the dies. Prior to a cutting, the streets 237 may be etched to a particular depth to help guide a saw blade. Furthermore, one or more side marks along the edge of the top of the memory wafer 203 and/or the logic wafer 205 can be used to align the saw blade before cutting. In many cases, and as illustrated by FIGS. 2A-2B, the dies can be formed on the memory wafer 203 and/or the logic wafer 205 such that the streets 237 are formed in perpendicular rows and columns.

The dies can comprise electronic devices, such as transistors, capacitors, diodes, memory devices, processors, other devices, and/or integrated circuits. In some embodiments, each die on a particular wafer can be a same type of device. For example, each die 202 of the memory wafer 203 can be a memory die (e.g., the memory die 102 described in association with FIG. 1) and each die 204 on the logic wafer 205 can be a logic die (e.g., the logic die 104). Non-limiting examples of the logic dies include application specific integrated circuits (ASICs) such as a DLA, a radio frequency communication circuit, a gene sequencing circuit, a video or imaging circuit, and audio circuit, a sensor circuit, a radar circuit, packet routing circuit, intrusion-detection circuit, safety monitoring circuit, cryptographic circuit, blockchain circuit, smart sensor circuit, 5G communication circuit, etc.

The memory dies 202 can include an array of memory cells (e.g., the memory array 110) resident on a die or chip. One or more of the memory dies 202 can include local input/output (LIO) lines for communication of data. Communication of data between the memory die 202 and the logic die 204 can be controlled by transceivers, which can be located on the memory die 202 and/or the logic die 204. In some embodiments, the electrical pathways by which signals indicative of data are communicated between the memory die 202 and the logic die 204 are also coupled to transceivers that control whether such data continues on an electrical pathway of a receiving device. As used herein, "receiving device" refers to a destination of signaling between the memory die 202 and the logic die 204. For example, a receiving device of signaling indicative of data from the memory die 202 to the logic die 204 is the logic die (or one or more logic devices formed thereon). When one or more of the transceivers are on, signals indicative of data from electrical pathways coupled to the transceiver are received by the receiving device, meaning that the signals pass through the transceiver and continue within the receiving device. When one or more transceivers are off, signals indicative of data from electrical pathways coupled to the transceiver are not received by the receiving device, meaning that the signals do not pass through the transceiver and continue within the receiving device. Non-limiting examples of an electrical pathway include a global data bus and an LIO line. The memory dies 202 can include transceivers associated with (e.g., coupled to) the LIO lines. The transceivers can therefore selectively enable communication of signals indicative of data between the memory die 202 and the logic die 204. The transceivers are discussed further in association with FIGS. 7A-7B.

Put in the context of an example operation, the memory die 202 can execute a read operation for data stored in memory cells. Signals indicative of the data can pass from the memory cells, through sensing circuitry, along LIOs, to a global data bus and to a host (if the host requested the data). The signals can also pass from the LIOs via the memory-to-logic circuitry 222 (described in association with FIG. 2C), through the wafer-on-wafer bond 211 (described in association with FIG. 2C) to the logic-to-memory circuitry 224 (described in association with FIG. 2C). If a transceiver in the logic-to-memory circuitry is on, the signals indicative of data can pass to the logic die 204, to be operated thereon by one or more logic devices. If the transistor is off, the signals indicative of data would not pass to the logic die 204. With respect to the operation of the memory die 202, in some embodiments, there is no functional difference in a read operation for data that is intended to be transferred to an external host versus for data that is intended to be transferred to the logic die 204. The read operation can progress normally and the transceivers associated with the logic die 204 can control whether or not the logic die will receive the data. Transfer of data from the memory die 202 to the logic die 204 is not limited to read operations, as described in more detail below. For example, other operations such as test mode operations and refresh operations can be used to transfer data from the memory die 202 to the logic die 204.

In some previous approaches, after fabrication of electronic devices on wafers, the wafers may be singulated (e.g., diced by a rotating saw blade cutting along streets). In contrast, in some embodiments of the present disclosure, after fabrication of electronic devices on the memory wafer 203 and/or the logic wafer 205, but prior to dicing, the memory wafer 203 and/or the logic wafer 205 can be bonded together by a wafer-on-wafer bonding process. Subsequent to the wafer-on-wafer bonding process, dies of the memory wafer 203 and/or the logic wafer 205 can be singulated (e.g., diced by a rotating saw blade cutting along streets). As described herein, the memory wafer 203 can be bonded to the logic wafer 205 in a face-to-face arrangement.

In some embodiments, the size of the electronic devices of the memory wafer 203 can be the same as the size of the electronic devices of the logic wafer 205. The streets 237 on the memory wafer 203 can be in a same relative position as the streets 237 on the logic wafer 205. This enables individual memory dies and logic dies to be singulated together as a single package after the memory wafer 203 and/or the logic wafer 205 are bonded together.

Although not specifically illustrated, in some embodiments, the size of the electronic devices of the memory wafer 203 and the logic wafer 205 can be proportionally different. For example, one logic die can have the same or similar footprint as 4 of the memory dies. After the memory wafer 202 and/or the logic die 204 are bonded together, the 4 memory dies and the logic die can be singulated as a single package. Conversely, one memory die can have the same footprint as 4 of the logic dies and the 4 logic dies and the memory die can be singulated as a single package. Such a package may be referred to as a network-on-wafer package. Embodiments are not limited to a 4:1 ratio of die sizes.

Figure 2C:
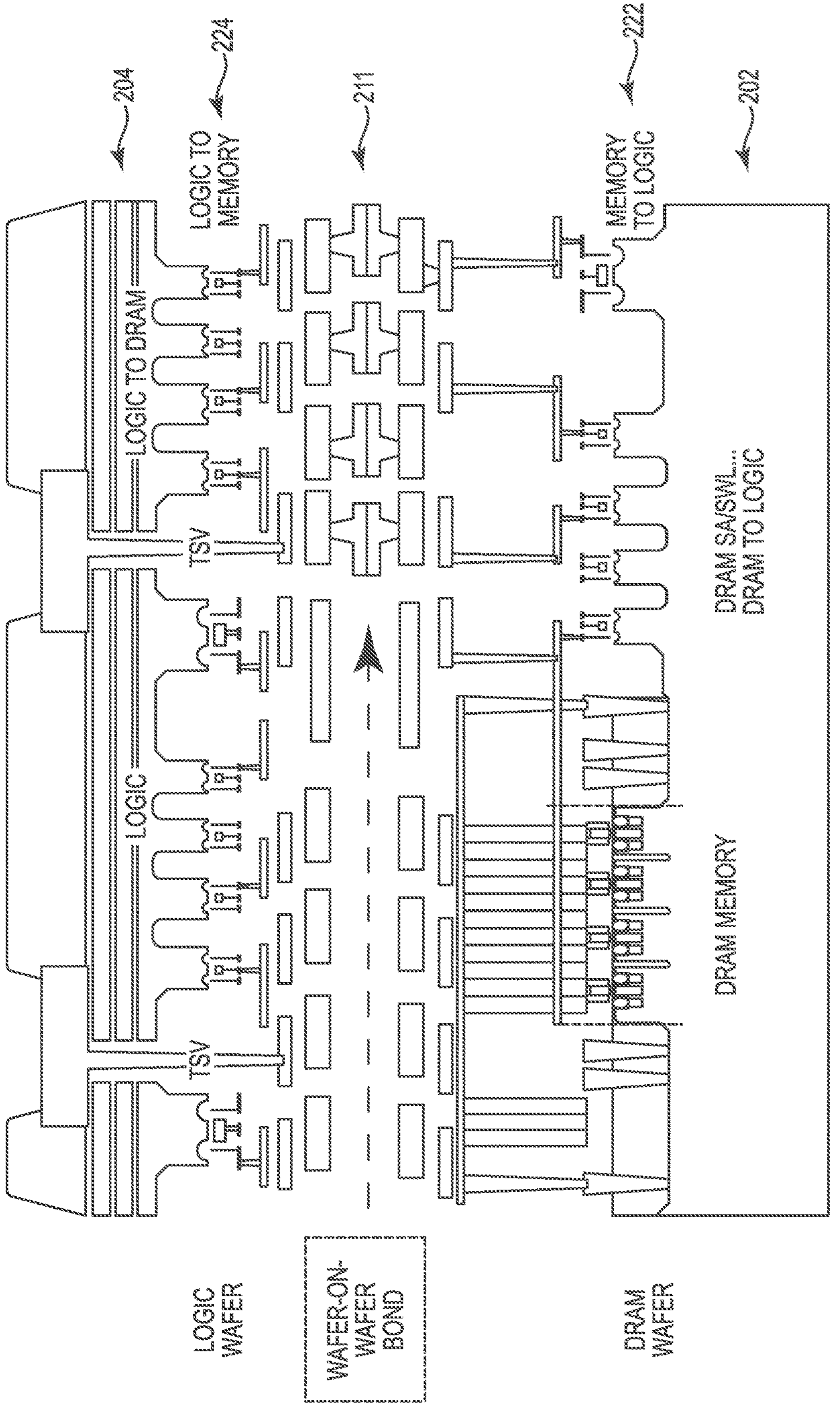
FIG. 2C is a cross-section of a portion of a memory die and a logic die with a wafer-on-wafer bond in accordance with a number of embodiments of the present disclosure.

FIG. 2C is a cross-section of a portion of a memory die 202 and a logic die 204 with a wafer-on-wafer bond 211 in accordance with a number of embodiments of the present disclosure. The memory die 202 and the logic die 204 can be analogous to the memory die 102 and the logic die 104, respectively, described in association with FIG. 1.

In some embodiments, the memory die 202 can include memory-to-logic circuitry 222 formed thereon. The memory-to-logic circuitry 222 can provide an electrical connection and signaling for the transfer of data and/or control signals between one or more memory arrays (e.g., the memory array 110) of the memory die 202 and one or more logic dies bonded thereto (e.g., the logic die 204). In some embodiments, the memory-to-logic circuitry 222 can include as few as two additional metal layers to those of the memory die 202.

In some embodiments, the logic die 204 includes logic-to-memory circuitry 224 formed thereon. The logic-to-memory circuitry 224 can provide an electrical connection and signaling for the transfer of data and/or control signals between one or more DLAs (e.g., the DLA 117) of the logic die 204 and one or more memory dies bonded thereto (e.g., the memory die 202).

A wafer-on-wafer bond 211 can be formed between the memory die 202 and the logic die 204. As illustrated by FIG. 2C, in some embodiments, the wafer-on-wafer bond 211 is formed between the memory-to-logic circuitry 222 and the logic-to-memory circuitry 224. The wafer-on-wafer bond 211 can include one or more of a metal bond and/or direct dielectric-dielectric bond. The wafer-on-wafer bond 211 can enable the transmission of electrical signals between the memory die 202 (e.g., via the memory-to-logic circuitry 222) and the logic die 204 (e.g., via the logic-to-memory circuitry 224).

The memory-to-logic circuitry 222 and/or the wafer-on-wafer bond 211 can include bond pads at transceivers of the logic-to-memory circuitry 224. The transceivers can be associated with an LIO prefetch bus and/or a sense amplifier (sense amp) stripe. In some embodiments, a sense amp stripe can include 188 LIO connection pairs covering 9 array cores and 9,216 pairs per channel. In some embodiments, a sense amp stripe can include 288 LIO connection pairs and 4608 pairs per channel. However, embodiments are not so limited.

The interconnect load of the wafer-on-wafer bond 211 can be less than 1.0 femtofarads and 0.5 ohms. In some embodiments, the maximum number of rows of memory capable of being activated at one time (e.g., 32 rows) can be activated and transmit data via the wafer-on-wafer bond 211 to the logic die 204. The memory-to-logic circuitry 222 and/or the wafer-on-wafer bond 211 can include a power connection and a ground connection for each transceiver. The power connection can enable activation of multiple rows of memory at once. The wafer-on-wafer bond 211 can provide *256k* data connections at a 1.2 micrometer pitch, for example.

In some embodiments, the wafer-on-wafer bond 211 can include analog circuitry (e.g., jumpers) without transistors in a data path between a memory die and a logic die. A memory die can drive a signal therebetween and a logic die can sink the signal therebetween, and vice versa. Instead of passing signals between a memory die and a logic die via logic gates, signals are transmitted directly between memory dies and logic dies. In some embodiments, the wafer-on-wafer bond 211 can be formed by a low temperature (e.g., room temperature) bonding process. In some embodiments, the wafer-on-wafer bond 211 can be further processed with an annealing step (e.g., at 300 degrees Celsius).

Although not specifically illustrated, a redistribution layer can be formed between the memory die 202 and the logic die 204. The redistribution layer can enable compatibility of a single memory design to multiple ASIC designs. The redistribution layer can enable memory technologies to scale without necessarily scaling down the logic design at the same rate as the memory technology. For instance, circuitry of the memory die 202 can be formed at a different resolution than circuitry of the logic die 204 without having to adjust the wafer-on-wafer bond 211 and/or other circuitry between the memory die 202 and the logic die 204.

Figure 2D:
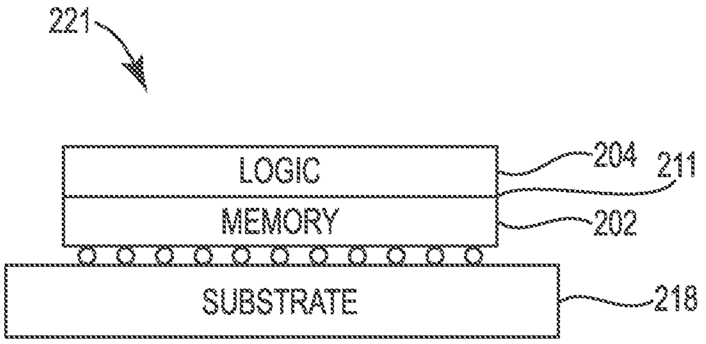
FIG. 2D illustrates a portion of a memory die and a logic die with a wafer-on-wafer bond after singulating in accordance with a number of embodiments of the present disclosure.

FIG. 2D illustrates a portion 221 of a memory die 202 and a logic die 204 with a wafer-on-wafer bond 211 after singulating in accordance with a number of embodiments of the present disclosure. The memory die 202 is illustrated as being bonded to a substrate 218. However, in some embodiments, the logic die 204 can be bonded to the substrate 218 instead of the memory die 202. The substrate 218, memory die 202, wafer-on-wafer bond 211, and logic die 204 can form a unit, such as an integrated circuit, configured to perform one or more desired functions. Although not specifically illustrated, the substrate 218 can include additional circuitry to operate, control, and/or communicate with the memory die 202, logic die 204, and/or other off-chip devices.

Although functionality of the memory die 202 may not change for memory operations, data can alternatively be transferred from the memory die 202 to the logic die 204 directly via the wafer-on-wafer bond 211 instead of being routed through 10 circuitry off of the memory die 202 (e.g., to an external host device). For example, a test mode and/or refresh cycle of the memory die 202 can be used to transfer data to and from the logic die 204 via the wafer-on-wafer bond 211 (e.g., via LIO lines of the memory die 202). Using the refresh cycle for an example, in some previous approaches, a DRAM memory device, with 8 rows per bank active and a refresh cycle time of 80 nanoseconds (versus 60 nanoseconds for a single row) with 4 banks in parallel and 16 nanosecond bank sequencing, the bandwidth would be 443 gigabytes/second. In contrast, in some embodiments of the present disclosure, with the wafer-on-wafer bond 211, a DRAM memory device, with 32 rows per bank active, the refresh cycle time can approach 60 nanoseconds for 32 banks in parallel and without bank sequencing, the bandwidth is 5 terabytes/second using 8 watts. Although such a significant bandwidth (e.g., 5 terabytes/second) of data from a memory device may overwhelm other interfaces and/or host device, logic devices, such as a DLA, can utilize such data bandwidth via connections provided by the wafer-on-wafer bond 211. Reducing off-chip movement of data can reduce power consumption associated with operating a memory device to provide significant data bandwidth.

Although not specifically illustrated, multiple memory dies 202 can be stacked on one another via a bond analogous to the wafer-on-wafer bond 211. Such additional memory dies 202 can include memory-to-memory circuitry analogous to the memory-to-logic circuitry 222 described in association with FIG. 2C. Alternatively, or additionally, TSVs can be used for communication of data between or through a stack of memory dies 202. Pads between stacked memory dies 202 can be at locations replicated on the stacked memory dies 202 in a vertical orientation (as illustrated) such that the stacked memory dies 202 are in alignment. The stacked memory dies 202 can be formed by a conventional process and/or by wafer-on-wafer bonding (between two memory dies 202) in different embodiments.

Although not specifically illustrated, a wafer bonded to the substrate 218 (e.g., the memory die 202 (as illustrated) or the logic die 204) can include TSVs formed therein to enable communication with circuitry external to the wafer. The TSVs can also be used to provide power and ground contacts. TSVs generally have greater capacitance and a larger pitch than a wafer-on-wafer bond but do not provide as great of a bandwidth as a wafer-on-wafer bond.

Although not specifically illustrated, in some embodiments, an additional component can be bonded to the portion 221. For example, a thermal solution component can be bonded to the top of the logic die 204 to provide cooling. The wafer-on-wafer bond 211 puts the logic die 204 and the memory die 202 in close proximity such that heat can be generated. A thermal solution component can help dissipate the generated heat. In some embodiments, a non-volatile memory component can be included to persistently store a model for an ANN, for example. However, in some embodiments, the non-volatile memory may not be necessary because a model may not need separate or large storage space and may be updated frequently.

Figure 3:
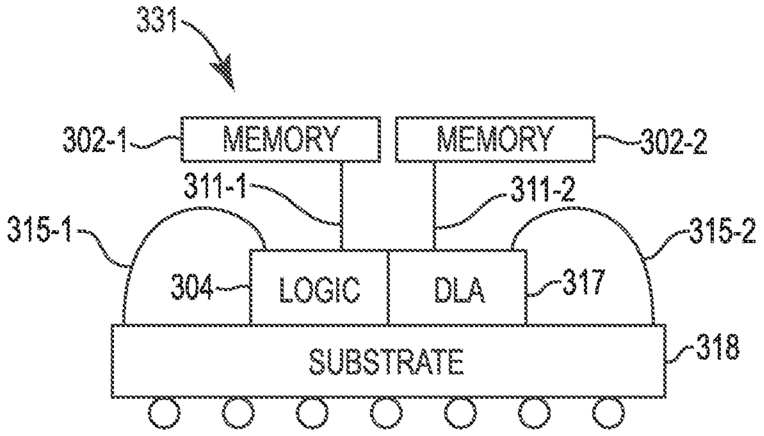
FIG. 3 illustrates a portion of two memory dies and a logic die in accordance with a number of embodiments of the present disclosure.

FIG. 3 illustrates a portion 331 of two memory dies 302-1 and 302-2 and a logic die 304 in accordance with a number of embodiments of the present disclosure. The memory dies 302-1 and 302-2 and logic die 304 can be analogous to the memory die 102 and logic die 104, respectively, described in association with FIG. 1. In the example of FIG. 3, the two lines 311-1 and 311-2 reflect separate connections between the memory die 302-2 and the DLA 317 and between the memory die 302-1 and circuitry of the logic die 304 other than the DLA 317. The connection represented by the line 311-1 can be the same type of connection as or a different type of connection than the connection represented by the line Although the DLA 317 is illustrated as a separate or distinct component from the logic die 304, in some embodiments, the DLA 317 is a component of the logic die 304. Illustrating the DLA 317 as separate or distinct from the logic die 304 is intended to distinguish the DLA 317 from other components or circuitry of the logic die 304.

The arrangement of the memory dies 302-1 and 302-2, the logic die 304, and the DLA 317 as illustrated in FIG. 3 can provide flexibility during fabrication. A memory die that is communicatively coupled to the DLA 317 (e.g., the memory die 302-2) can have different operating and/or performance requirements than another memory die (e.g., the memory die 302-1) that is not communicatively coupled to the DLA 317. As such, during fabrication, one or more memory dies that are to be communicatively coupled to the DLA 317 can be selected (from a pool of memory dies, for example) based on a performance metric. Examples of the performance metric include results of testing, raw bit error rate, inputs/outputs per second, etc.

As an illustrative example, whether a prospective memory die (selected from a pool of memory dies, for example) is communicatively coupled to the DLA 317 or communicatively coupled to circuitry of the logic die 304 other than the DLA 317 can be determined based on a value of a performance metric of the prospective memory die. In some embodiments, if the value of the performance metric of a prospective memory die satisfies a threshold value the performance metric, then the prospective memory die can be the memory die 302-2. If the value of the performance metric of a prospective memory die does not satisfy a threshold value of the performance metric, then the prospective memory die can be the memory die 302-1. In some embodiments, if a prospective memory die has a value of a performance metric that is more preferred than a value of the performance metric of another prospective memory die (selected from the same pool of memory dies, for example), then the prospective memory die can be the memory die 302-2 and the other prospective memory die can be the memory die 302-1.

In some embodiments, circuitry of the logic die 304, other than the DLA 317, can manage the memory die 302-1. In some embodiments, there may not be direct communication of signaling between the memory dies 302-1 and 302-2 and the substrate 318. Rather, signaling between the memory dies 302-1 and 302-2 and the substrate 318 is handled by circuitry of the logic die 304 (which can include the DLA 317), as indicated by jumpers 315-1 and 315-2.

FIG. 3 illustrates the logic die 304 and the DLA 317 being bonded to a substrate 318. However, in at least one embodiment, the memory dies 302-1 and 302-2 can be bonded to the substrate 318 instead of the logic die 304 and the DLA 317. Although not specifically illustrated, the substrate 318 can include circuitry to operate, control, and/or communicate with the memory dies 302-1 and 302-2, the logic die 304, and/or other off-chip devices. Although FIG. 3 is described with two memory dies coupled to the logic die 304, embodiments of the present disclosure are not so limited. For example, more than one memory die can be coupled to the DLA 317 and/or more than one memory die can be coupled to the logic die 304. In some embodiments, three memory dies having respective more preferred values of a performance metric can be communicatively coupled to the DLA 317 and a memory die having a less preferred value of the performance metric can be coupled to circuitry of the logic die 304 other than the DLA 317.

Figure 4:
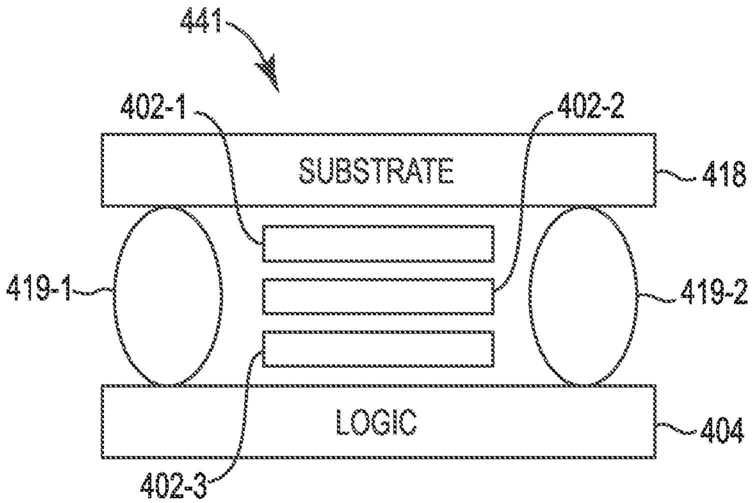
FIG. 4 illustrates a portion of a stack of memory dies and a logic die in accordance with a number of embodiments of the present disclosure.

FIG. 4 illustrates a portion 441 of a stack of memory dies 402-1, 402-2, and 402-3 and a logic die 404 in accordance with a number of embodiments of the present disclosure. The memory dies 402-1, 402-2, and 402-3 and the logic die 404 can be analogous to the memory die 102 and the logic die 104, respectively, described in association with FIG. 1. Although not specifically illustrated, the substrate 418 can include circuitry to operate, control, and/or communicate with the memory dies 402-1, 402-2, and 402-3, logic die 404, and/or other off-chip devices.

In the example of FIG. 4, multiple memory dies 402-1, 402-2, and 402-3 are stacked between the logic die 404 and the substrate 418. The memory dies 402-1, 402-2, and 402-3 are stacked vertically. In-plane bump contacts 419-1 and 419-2 couple the logic die 404 to the substrate 418. In some embodiments, a ball grid array (BGA) can be formed on the substrate 418 prior to coupling the stack of the memory dies 402-1, 402-2, and 402-3 and/or the logic die 404 to the substrate 418. Thus, the in-plane bump contacts 419-1 and 419-2 can be a portion of a BGA formed on the substrate 418.

Figure 5:
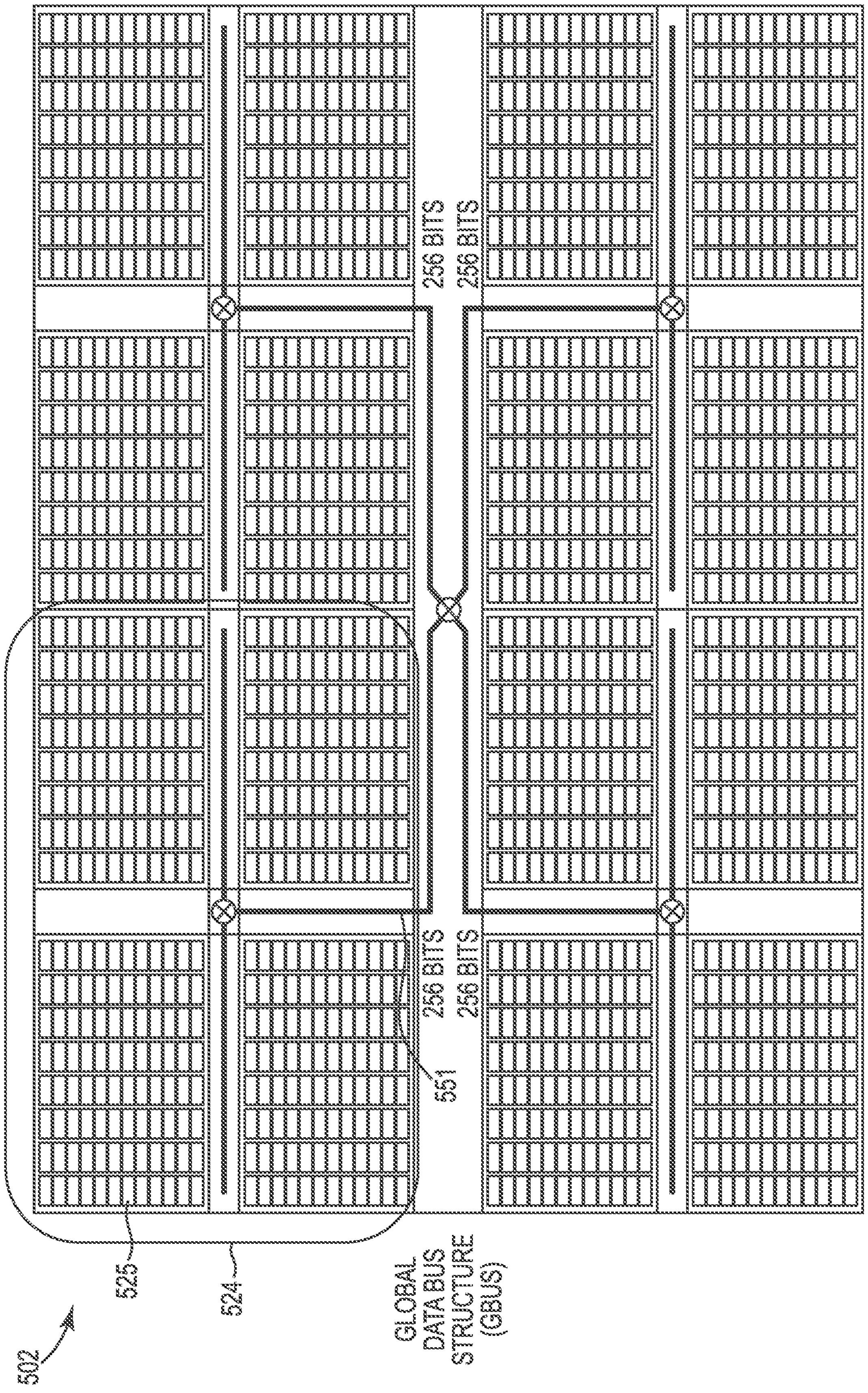
FIG. 5 illustrates a circuit diagram of a memory die in accordance with a number of embodiments of the present disclosure.

FIG. 5 illustrates a circuit diagram of a memory die 502 in accordance with a number of embodiments of the present disclosure. The memory die 502 includes 16 memory banks 525 arranged in bank groups 524 of 4 banks. Each bank group 524 is coupled to a global data bus 551 (e.g., a 256 bit wide bus). Embodiments are not limited to these specific examples. The global data bus 551 can be modeled as a charging/discharging capacitor. The global data bus 551 can conform to a memory standard for sending data from the memory die 502 via an IO bus. However, although not specifically illustrated in FIG. 5, in some embodiments, a logic die coupled to the memory die 502 via a wafer-on-wafer bond can include transceivers for communicating data from the memory die 502 to the logic die via the wafer-on-wafer bond.

Figure 6:
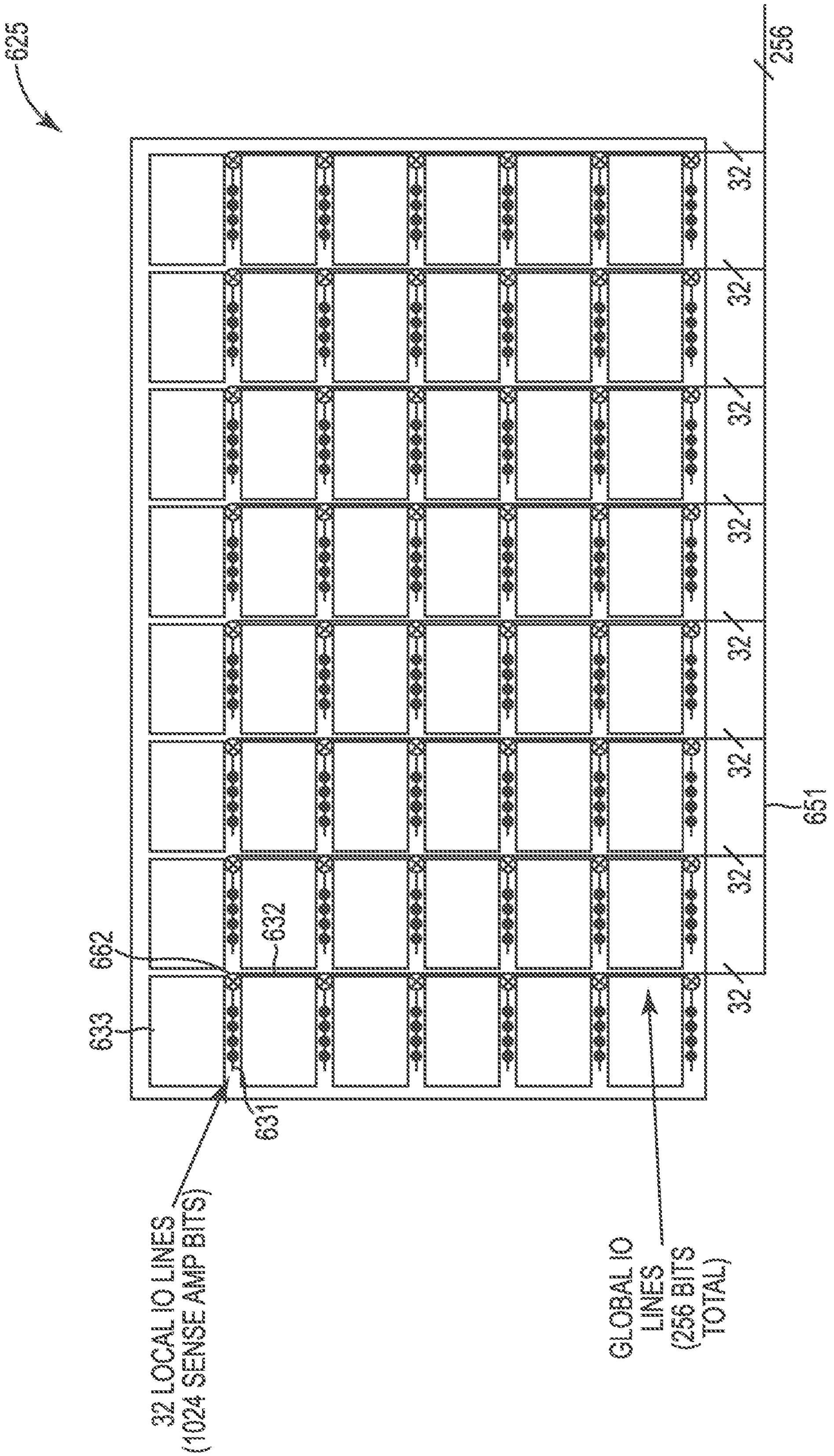
FIG. 6 illustrates a circuit diagram of a memory bank in accordance with a number of embodiments of the present disclosure.

FIG. 6 illustrates a memory bank 625 in accordance with a number of embodiments of the present disclosure. The memory bank 625 includes a quantity of memory devices 633, each including a quantity of rows and a quantity of columns of memory cells (e.g., 1024×1024). Each memory device 633 can include a respective quantity of LIO lines 631 represented by the filled dots. For example, each tile can include 32 LIO lines 631. The LIO lines 631 in each tile are coupled to a global IO line 632 via a multiplexer 662. The multiplexer 662 may also be referred to in the art as a transceiver, but is referred to herein as a multiplexer to differentiate from transceivers of the logic die configured to receive signals from the LIO lines 631, the global IO lines 632, and/or the global data bus 651.

The multiplexers 662 can be configured to receive signals from the LIO lines 631. The multiplexers 662 select a portion of the LIO lines 631. The multiplexers 662 can amplify the signals received from the selected portion of the LIO lines 631. The multiplexers 662 can also cause the amplified signals to be transmitted via the global IO lines 632. The multiplexers 662 can also receive signals from the global IO lines 632 and reduce the received signals. The multiplexers 662 can further transmit the reduced signals to the LIO lines 631.

The global IO lines 632 are coupled to the global data bus 661. Signals from multiple sense amplifiers can be multiplexed into the LIO lines 631. The LIO lines 631 can be coupled to the multiplexers 662 and transceivers (not shown) of the logic die via a wafer-on-wafer bond. The transceivers (not shown) of the logic die can cause signals from the LIO lines 631 to be received by the logic die via the wafer-on-wafer bond. The wafer-on-wafer bond provides pitch control sufficiently fine to allow for contacts between the transceivers (not shown) and the LIO lines 631, which would otherwise not be possible.

In some embodiments, the transceiver (not shown) of the logic die can receive an enable/disable command from the corresponding logic die (e.g., as opposed to receiving the command from a host). In some embodiments, the enable/disable command can be received by multiple transceivers of the logic die (e.g., the enable/disable command can cause signals indicative of data from a particular row in each memory bank 625 to be transferred via the corresponding transceivers). The control and operation of the multiple transceivers of the logic die is similar to having thousands of memory controllers, except that they transfer data rather than controlling all operations. Such operation can be beneficial, for example, for applications that involve massively parallel memory access operations. For an example memory device that is configured to include an 8 kilobit row, 256 bits of data can be prefetched per transceiver of the logic die. Therefore, each transceiver of the logic die can have 256 bits bonded out. In other words, some embodiments can transfer 256 bits of data for each 8 kilobits of stored data (in this example architecture). In contrast, according to some previous approaches with an analogous architecture, a typical memory interface (e.g., via a global IO line) would only be able to transfer 256 bits for 4 gigabits of stored data.

Figure 7A:
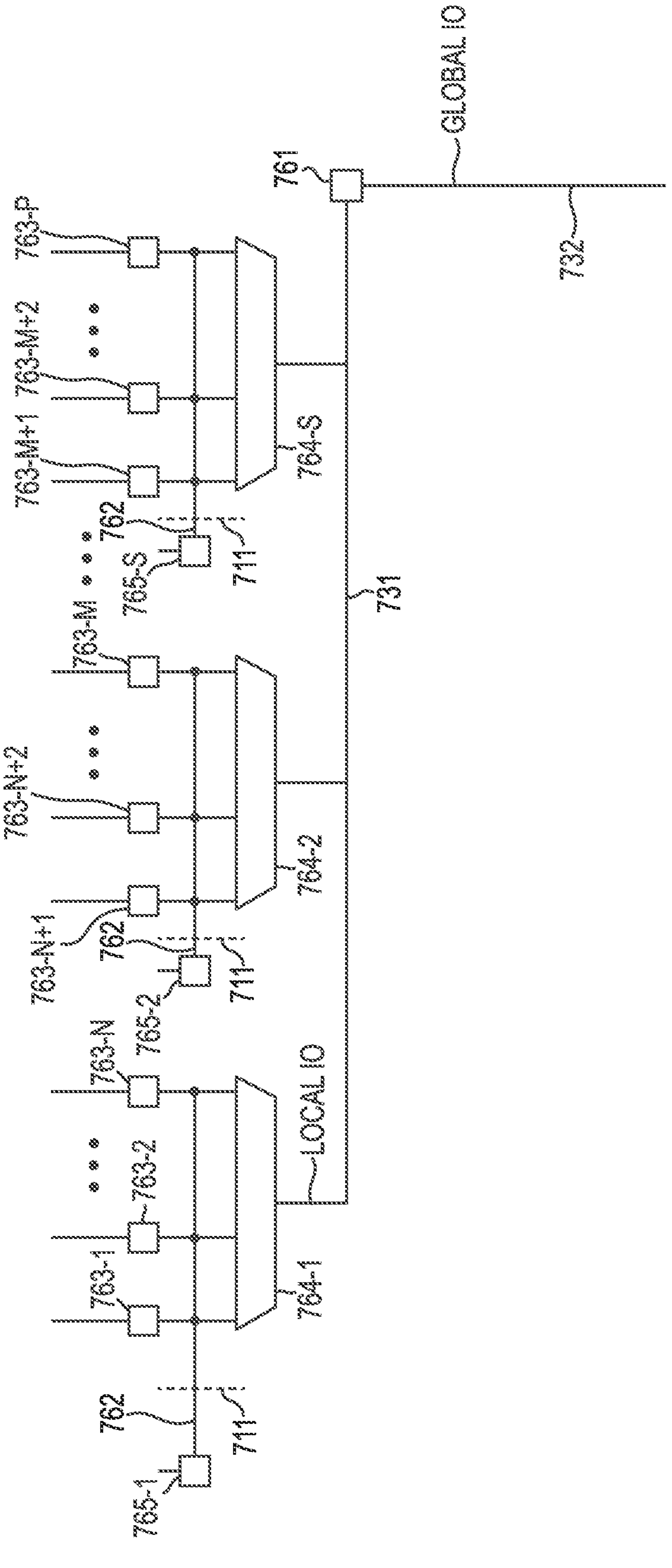
FIG. 7A illustrates a circuit diagram of sense amplifiers and multiplexers in accordance with a number of embodiments of the present disclosure.

FIG. 7A illustrates a circuit diagram of sense amplifiers 763-1, 763-2, . . . , 763-N, 763-N+1, 763-N+2, . . . , 763-M, 763-M+1, 763-M+2, . . . , 763-P and multiplexers 764-1, 764-2, . . . , 764-S in accordance with a number of embodiments of the present disclosure. The sense amplifiers 763-1, 763-2, . . . , 763-N, 763-N+1, 763-N+2, . . . , 763-M, 763-M+1, 763-M+2, . . . , 763-P can be referred to as sense amplifiers 763. The multiplexers 764-1, 764-2, . . . , 764-S can be referred to as multiplexers 764. FIG. 7A also includes the multiplexer 761 of the memory die. For clarity, FIG. 7A has been simplified to focus on components and circuitry of a memory die and a logic die with particular relevance to the present disclosure.

The multiplexer 761 is differentiated from the transceivers 765-1, 765-2, . . . , 765-S. The multiplexer 761 can be configured to receive signals from the LIO lines 731. The multiplexer 761 selects a portion of the LIO lines 731. The multiplexer 761 can amplify the signals received from the selected portion of the LIO lines 731. The multiplexer 761 can also cause the amplified signals to be transmitted via the global IO lines 732. The multiplexer 761 can also receive signals from the global IO lines 732 and reduce the received signals. The multiplexer 761 can further transmit the reduced signals to the LIO lines 731. Although the multiplexer 761 is referred to as a multiplexer, the multiplexer 761 is different than the multiplexers 764 and has different functions than the multiplexers 764.

The transceivers 765-1, 765-2, . . . , 765-S can also receive signals, select a portion of the signals, amplify the portion of the signals, and transmit the amplified signals. However, the transceivers 765-1, 765-2, . . . , 765-S can transmit the amplified signals to the logic die and not the global IO lines 732.

The memory die can include the sense amplifiers 763, the multiplexers 764, and the multiplexer 761. The memory die can also include a LIO 731 and a global IO line 732. In various examples, a wafer-on-wafer bond 711 can couple the output of the sense amplifiers 773 to the transceivers 765 of the logic die. The transceivers 765 can be controlled by the logic die to cause the output of the sense amplifiers 763 to be provided to circuitry of the logic die. For example, a transceiver 765-1 can cause signals outputted from the sense amplifiers 763-1, 763-2, . . . , 763-N to be provided to circuitry of the logic die that is downstream from the transceiver 765-1. Although a single transceiver 765-1 is shown, the transceiver 765-1 can represent multiple transceivers such that each of the outputs of the sense amplifiers 763-1, 763-2, . . . , 763-N is provided concurrently to the circuitry downstream from the multiple transceivers of the logic die. The transceivers 765-2 can cause the output of the sense amplifiers 763-N−1, 763-N+2, . . . , 763-M to be provided to circuitry of the logic die. The transceivers 765-S can cause the output of the sense amplifiers 763-M+1, 763-M+2, . . . , 763-P to be provided to circuitry of the logic die.

Control circuitry of the logic die (e.g., the control circuitry 118 described in association with FIG. 1) can send a signal to the transceivers 765, to selectively route the signals representing data off-chip (e.g., to the logic die). The illustrated path from the sense amplifiers 763 to the transceivers 765 of the logic die is a representation of the electrical pathway between the memory die and the logic die. Embodiments of the present disclosure can preserve the functionality and fabrication of a standardized memory interface while allowing for the functionality and fabrication of an additional high bandwidth interface from the memory die to the logic die via the wafer-on-wafer bond 711.

In various examples, each of the transceivers 765 can be coupled to a plurality of sense amplifiers 763. For example, the transceiver 765-1 can be coupled to the sense amplifiers 763-1, 763-2, . . . , 763-N. The transceiver 765-2 can be coupled to the sense amplifiers 763-N+1, 763-N+2, . . . , 763-M. The transceiver 765-S can be coupled to the sense amplifiers 763-M+1, 763-M+2, . . . , 763-P. In various instances, each of the transceivers 765 can direct a plurality of signals. For example, the transceiver 765-1 can direct the signals provided from the sense amplifiers 763-1, 763-2, . . . , 763-N at a same time. The transceiver 765-2 can redirect the signals provided from the sense amplifiers 763-N+1, 763-N+2, . . . , 763-M at a same time. The transceiver 765-S can direct signals provided from the sense amplifiers 763-M+1, 763-M+2, . . . , 763-P at a same time.

Control circuitry of the logic die can cause signals representing data to be received at the logic die from a typical IO path including the LIOs 731 utilizing the transceiver 765. Control circuitry of the memory die (e.g., the control circuitry 116 described in association with FIG. 1) can cause signals representing data to be provided through a typical input/output path utilizing the LIOs 731, the multiplexer 761, and the global IO line 732. In various instances, the transceivers 765 can route signals concurrently. For example, the transceiver 765-1 can route signals between the sense amplifiers 763-1, 763-2, . . . , 763-N and the logic die concurrently with the routing of signals by the transceiver 765-2, . . . , and/or transceiver 765-S. In various examples, the transceiver 765-1 can route signals between the sense amplifiers 763-1, 763-2, . . . , 763-N and the logic die concurrently.

Although not shown, the transceivers of the logic die coupled to multiple memory devices can route signals from the memory die to the logic die concurrently. For example, the transceivers 765 can route data with other transceivers coupled to different memory devices concurrently. Control circuitry can activate rows of multiple memory devices concurrently to cause corresponding sense amplifiers (e.g., including sense amplifiers 763) to latch signals. The transceivers (e.g., including the transceivers 765) coupled to different memory devices can route signals from the sense amplifiers of the memory devices to the logic die concurrently. The logic die can concurrently receive a greater quantity of signals from the memory die via the transceivers 765 than would be possible to output via the global IO lines 732 or a global bus. Similarly, the logic die can provide a greater quantity of signals concurrently to the memory die via the transceivers 765 than would be possible via the global IO lines 732 or a global bus. The transceivers 765 can route signals concurrently with the routing of data by transceivers coupled to different banks via the wafer-on-wafer bond 711. In various examples, the memory die can output data to the global IO lines 732 and the transceivers 765 concurrently. For example, control circuitry of the memory die can activate the LIOs 731 and the global IO lines 732 concurrently with the activation of the transceivers 765, by control circuitry of the logic die, to output signals to the logic die and to output signals through the traditional IO circuitry, which includes global IO lines 732.

In various instances, signals can be provided from a global bus of the memory die to the logic die. A transceiver of the logic die, coupled to the global bus, can be configured to route data from the memory die to the logic die. For example, the transceiver of the logic die can be activated to route signals from the global bus to the logic die. The transceivers configured to route signals from the global bus to the logic die can be different than the transceivers configured to route signals from the LIO lines 731 to the logic die. Two independent paths can be provided for routing signals from the memory die to the logic die. The first path can originate at the LIO lines 731. The second path can originate at the global bus of the memory die. The first path can be utilized by activating one or more transceivers of the logic die. The second path can be utilized by activating one or more different transceivers of the logic die. In various instances, the quantity of signals that can be routed concurrently from the LIO lines 731 to the logic die can be greater than the quantity of signals that can be routed concurrently from the global bus to the logic die.

Figure 7B:
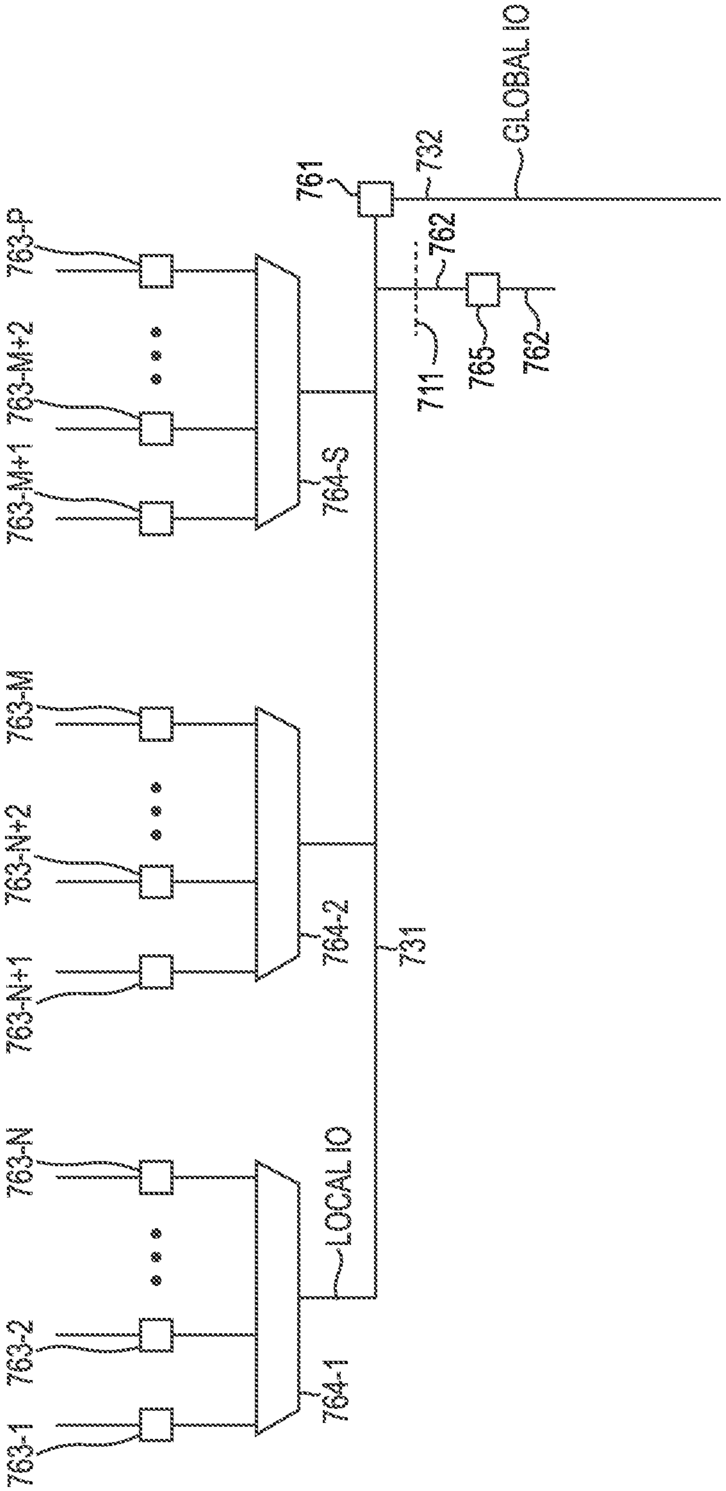
FIG. 7B illustrates a circuit diagram of a local input output (LIO) line in accordance with a number of embodiments of the present disclosure.

FIG. 7B illustrates a circuit diagram of a LIO line 731 in accordance with a number of embodiments of the present disclosure. In FIG. 7B the transceiver 765 is coupled to the LIO line 731 as compared to FIG. 7A in which the transceivers 765 are coupled to the sense amplifiers 763.

In FIG. 7B, the sense amplifiers 763 can output a plurality of signals. The signals can be output to the multiplexers 764. For example, the sense amplifiers 763-1, 763-2, . . . , 763-N can output a first plurality of signals to the multiplexer 764-1. The sense amplifiers 763-N+1, 763-N+2, . . . , 763-M can output a second plurality of signals to the multiplexer 764-2 while the sense amplifiers 763-M+1, 763-M+2, . . . , 763-P can output an Sth plurality of signals to the multiplexer 764-S. As used herein, "Sth" represents a variable such that "Sth plurality of signals" represents a variable plurality of signals.

Each of the multiplexers 764 can output a plurality of signals to the LIOs 731. For example, the multiplexer 764-1 can output a first portion of the first plurality of signals, the multiplexer 764-2 can output a second portion of the second plurality of signals, . . . , the multiplexer 764-S can output an Sth portion of the Sth plurality of signals.

The transceiver 765 can route the signals of the LIO lines 731 of the memory die to an LIO line 762 of the logic die, for example. In various examples, the memory die can activate the multiplexer 761 to output signals from the LIO lines 731 to the global IO lines 732 through a traditional IO circuitry of the memory device. The logic die can concurrently activate the transceiver 765 with the activation of the LIO lines 731 and the global IO lines 732 to output data to the logic die concurrent with outputting of the data via the IO circuitry of the memory die. For example, control circuitry of the memory device can determine whether to output data through the traditional IO circuitry of the memory device and control circuitry of the logic die can determine whether to output data to the logic die.

Although a single transceiver 765 is shown, a multiple transceivers can be utilized to route signals from multiple LIO lines of a memory die to the logic die. For example, a transceiver can be coupled to a LIO line of a memory device of the memory die. Another transceiver can be coupled to a LIO line of another memory device of the memory die. Each of the transceivers can route signals to the logic die by routing the signals to LIO lines 762 of the logic die. Each of the transceivers can route signals concurrently. In various instances, the transceiver 765 can be coupled to the global IO line 732 instead of the sense amplifiers 763 or the LIO line 731. Similarly, the transceivers coupled to the global IO lines can concurrently route signals to the logic die.

In some embodiments, first metal pads can be formed on a first wafer. Memory-to-logic circuitry can be formed on memory devices. The memory-to-logic circuitry can couple LIO lines of a memory device to a subset of the first metal pads, which can be dedicated to communication between the memory devices and logic devices via the memory-to-logic circuitry. A different subset of the first pads can be dedicated to communication external to the wafer-on-wafer bonded memory dies and logic dies. Second metal pads can be formed on a second wafer. Logic-to-memory circuitry can be formed on the logic devices.

A subset of the first metal pads can be bonded to a subset of the second metal pads via a wafer-on-wafer bonding process. Each memory device on the first wafer can be aligned with and coupled to one or more logic devices on the second wafer. A respective IO line of each of the memory devices can be coupled to an IO line of a respective logic device. Four memory devices on the first wafer can be aligned with and coupled to a respective logic device on the second wafer. Four memory devices and a logic device have a same footprint. Bonded first and second wafers can be singulated into individual wafer-on-wafer bonded memory and logic dies.

In some embodiments, a wafer-on-wafer bond can be formed between a first wafer having a memory die formed thereon and a second wafer having a logic die formed thereon. The wafer-on-wafer bond can provide data paths from the memory die directly to the logic die and couple IO lines to a DLA formed on the logic die. The memory die and the logic die can be in a face-to-face arrangement.

In some embodiments, a logic die having a DLA thereon can be coupled to a substrate. The DLA can be distinct from other circuitry of the logic die. A memory die, having a more preferred value of a performance metric, can be communicatively coupled to the DLA in a face-to-face arrangement. A value of a performance metric that satisfies a threshold value of the performance metric can be a more preferred value. Memory dies can be selected from a pool of memory dies. Another memory die, having a less preferred value of the performance metric, can be communicatively coupled to the other circuitry of the logic die in a face-to-face arrangement. A value of a performance metric that does not satisfy a threshold value of the performance metric can be a less preferred value. The memory die can be communicatively coupled to the DLA in response to determining that the memory die has the more preferred value and the other memory die can be communicatively coupled to the other circuitry of the logic die in response to determining that the other memory die has the less preferred value.

In some embodiments, a stack of memory dies, including a respective first memory die proximal to a substrate and a respective last memory die distal to the substrate, can be bonded to the substrate. A logic die can be bonded to the substrate with a plurality of bump contacts in-plane with the stack of memory dies. The logic die can be in contact with the respective last memory die. The plurality of bump contacts can couple the substrate to the logic die. The bump contacts can be a BGA on the substrate. A first surface of the respective last memory die can be bonded to another memory die of the stack of memory dies and a second surface of the respective last memory die, opposite the first surface, can be bonded to the logic die.

Although specific embodiments have been illustrated and described herein, those of ordinary skill in the art will appreciate that an arrangement calculated to achieve the same results can be substituted for the specific embodiments shown. This disclosure is intended to cover adaptations or variations of various embodiments of the present disclosure. It is to be understood that the above description has been made in an illustrative fashion, and not a restrictive one. Combinations of the above embodiments, and other embodiments not specifically described herein will be apparent to those of skill in the art upon reviewing the above description. The scope of the various embodiments of the present disclosure includes other applications in which the above structures and methods are used. Therefore, the scope of various embodiments of the present disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the disclosed embodiments of the present disclosure have to use more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed is:

1. An apparatus, comprising:

a first substrate;

a memory die formed on a second substrate comprising a first wafer, the memory die coupled to the first substrate on a first surface of the memory die, wherein the memory die includes a plurality of dynamic random access memory (DRAM) devices; and a logic die formed on a third substrate comprising a second wafer, the logic die coupled to the memory die on a second surface of the memory die opposite the first surface by a wafer-on-wafer bond between the first wafer and the second wafer, wherein the logic die includes a plurality of logic devices, wherein at least one of the plurality of logic devices comprises a deep learning accelerator (DLA), wherein the wafer-on-wafer bond couples at least one of the plurality of DRAM devices directly to the DLA;

wherein the first substrate is a different substrate than the second substrate;

wherein the second substrate is a different substrate than the third substrate;

wherein the third substrate is a different substrate than the first substrate; and wherein a test mode or a refresh cycle of the at least one of the plurality of DRAM devices is configured to communicate data values via local input/output lines of the at least one of the plurality of DRAM devices to and from the DLA via the wafer-on-wafer bond.

2. The apparatus of claim 1, wherein the memory die and the logic die are in a face-to-face arrangement.

3. The apparatus of claim 1, wherein the wafer-on-wafer bond comprises a metal material formed in contact with the memory die and the logic die.

4. The apparatus of claim 1, wherein the memory die further comprises a plurality of global input/output (IO) lines coupled to a plurality of local IO lines of the plurality of DRAM devices, and wherein the wafer-on-wafer bond couples the plurality of global IO lines directly to the DLA.

5. The apparatus of claim 4, wherein the logic die comprises a plurality of pads, and wherein the wafer-on-wafer bond couples respective ones of the plurality of global IO lines to the plurality of pads.

6. The apparatus of claim 1, wherein the wafer-on-wafer bond is further configured to communicate data values from more than one of the plurality of DRAM devices to the DLA in parallel.

7. The apparatus of claim 1, wherein the wafer-on-wafer bond comprises a first metal material of the logic die and a second metal material of the memory die.

8. The apparatus of claim 1, wherein the memory die further comprises memory-to-logic circuitry configured to provide paths for communication of data values from the plurality of DRAM devices directly to the DLA.

9. The apparatus of claim 8, wherein the wafer-on-wafer bond is in contact with the memory-to-logic circuitry.

10. The apparatus of claim 1, wherein the logic die further comprises logic-to-memory circuitry configured to:

receive first data values directly from the plurality of DRAM devices;

provide the first data values to the DLA; and provide second data values from the DLA to the plurality of DRAM devices.

11. The apparatus of claim 10, wherein the wafer-on-wafer bond is in contact with the logic-to-memory circuitry.

12. The apparatus of claim 1, wherein the apparatus comprises a digital signal processor (DSP), a graphics processing unit (GPU), or a system on chip (SoC).

13. The apparatus of claim 1, wherein the logic die comprises a plurality of vias directly coupled to the wafer-on-wafer bond.

14. The apparatus of claim 1, wherein the memory die and the logic die are singulated together as a single package from the first wafer and the second wafer subsequent to the wafer-on-wafer bond between the first wafer and the second wafer.

15. An apparatus, comprising:

a substrate;

a stack of memory dies bonded to the substrate, wherein the stack of memory dies comprises a first memory die proximal to the substrate and bonded to the substrate and a last memory die distal to the substrate; and a logic die bonded to the substrate with a plurality of bump contacts in-plane with the stack of memory dies, wherein the logic die is proximal to the last memory die and distal to the first memory die, and wherein the logic die is coupled to and in direct physical contact with the last memory die on a surface of the logic die.

16. The apparatus of claim 15, wherein the plurality of bump contacts comprise a ball grid array (BGA) on the substrate.

17. The apparatus of claim 15, wherein a first surface of the last memory die is bonded to another memory die of the stack of memory dies, and wherein a second surface of the last memory die, opposite the first surface, is bonded to the logic die.

* * * * *